(12) United States Patent
Bukhary

(10) Patent No.: US 8,529,252 B2
(45) Date of Patent: Sep. 10, 2013

(54) REVERSE HEADGEAR WITH NECK STRAP

(75) Inventor: Mohammed Taher Bukhary, Riyadh (SA)

(73) Assignee: King Saud University, Riyadh (SA)

( * ) Notice: Subject to any disclaimer, the term of this patent is extended or adjusted under 35 U.S.C. 154(b) by 76 days.

(21) Appl. No.: 13/216,168

(22) Filed: Aug. 23, 2011

(65) Prior Publication Data

US 2013/0052602 A1 Feb. 28, 2013

(51) Int. Cl.
*A61D 3/00* (2006.01)

(52) U.S. Cl.
USPC .............................................. 433/5

(58) Field of Classification Search
USPC ..................... 433/24, 5–6; 602/17
See application file for complete search history.

(56) References Cited

U.S. PATENT DOCUMENTS

| 3,401,457 | A | * | 9/1968 | Hickham | 433/5 |
| 3,423,832 | A | | 1/1969 | Nelson | |
| 3,514,860 | A | | 6/1970 | Stifer | |
| 4,115,921 | A | * | 9/1978 | Armstrong | 433/5 |
| 4,121,341 | A | * | 10/1978 | DeWoskin | 433/5 |
| 4,259,065 | A | * | 3/1981 | DeWoskin | 433/5 |
| 4,375,355 | A | * | 3/1983 | Dahan | 433/5 |
| 4,375,962 | A | * | 3/1983 | DeWoskin | 433/5 |
| 4,577,627 | A | * | 3/1986 | Facal Garcia | 606/204.15 |
| 4,600,382 | A | * | 7/1986 | Forster | 433/5 |
| 4,695,250 | A | * | 9/1987 | Mariol | 433/5 |
| 4,988,291 | A | | 1/1991 | Grummons | |
| 5,158,451 | A | * | 10/1992 | Pourcho | 433/5 |
| 5,203,694 | A | | 4/1993 | Klien | |
| 5,810,583 | A | | 9/1998 | Doyle | |
| 5,890,891 | A | | 4/1999 | Doylr | |
| 6,976,838 | B1 | | 12/2005 | Keles | |
| 7,011,642 | B2 | | 3/2006 | Greene et al. | |
| 7,090,489 | B2 | | 8/2006 | Akkaya | |
| 7,121,824 | B2 | | 10/2006 | Keles et al. | |
| 7,677,886 | B2 | | 3/2010 | Mitani | |
| 2006/0029899 | A1 | | 2/2006 | Keles | |

FOREIGN PATENT DOCUMENTS

WO WO 9743975 A1 11/1997

* cited by examiner

*Primary Examiner* — Cris L Rodriguez
*Assistant Examiner* — Hao D Mai
(74) *Attorney, Agent, or Firm* — Richard C. Litman

(57) ABSTRACT

The reverse headgear with neck strap has: a forehead-cap adapted to engage a patient's forehead; a chin-cap adapted to engage the patient's chin; and a frame interconnecting the forehead-cap and the chin-cap. The frame has side portions extending between the forehead-cap and the chin-cap defining rearward extending loops. A neck strap is releasably connected to the loops on opposite sides of the frame by hooks, the neck strap passing behind the patient's neck in order to apply a traction force to the chin cap to draw the mandible posteriorly. An M-shaped hook is attached to the chin-cap and extends in front of a mouth of the patient, the hook being configured to receive a tension applying elastic element attachable to the patient's upper teeth in order to apply anterior traction to the maxilla, thereby correcting a class III malocclusion by tensioning the maxilla forward and the mandible rearward.

11 Claims, 6 Drawing Sheets

REVERSE HEADGEAR WITH NECK STRAP

BACKGROUND OF THE INVENTION

1. Field of the Invention

The present invention relates to an orthodontic and orthopedic appliances for the correction of abnormal dental occlusions, and more particularly to a reverse headgear with neck strap that is adapted to simultaneously apply anterior traction force to the maxilla and posterior traction force to the mandible for the correction of class III malocclusions.

2. Description of the Related Art

A class III malocclusion generally refers to a condition in which the mandibular first molar extends anterior to the maxillar first molar, generally resulting in the lower front teeth extending forward of the upper front teeth. The malocclusion may result from a variety of causes, including skeletal abnormalities where the upper jaw is too short or the lower jaw is too long. Class III malocclusions may result in further dental problems, in TMJ or tempero-mandibular joint disease, and they may also result in cosmetic embarrassment, such as a distorted face or protruding lower jaw. Class III malocclusions may be treated by surgery, but surgery is expensive and may leave residual scars. More conservative treatments generally either concentrate on correcting the alignment of only the alignment of the maxilla or only the alignment of the mandible, or have mixed results.

There is a need for an orthodontic or orthopedic appliance for conservative treatment of class III malocclusions that simultaneously applies traction to both the maxilla and the mandible to correct the malocclusion. Thus, a reverse headgear with a neck strap solving the aforementioned problems is desired.

SUMMARY OF THE INVENTION

The reverse headgear with neck strap is an orthopedic appliance having: a forehead-cap adapted to engage a forehead of a patient; a chin-cap adapted to engage a chin of the patient; and a frame interconnecting the forehead-cap and the chin-cap. The frame has side portions extending between the forehead-cap and the chin-cap, the side portions each having a rearward extending loop between the forehead-cap and chin-cap. A neck strap is releasably connected to the loops on opposite sides of the frame by hooks, the neck strap being adapted to pass behind the neck of the patient in order to apply a traction force to the chin cap to draw the mandible posteriorly. An M-shaped hook is attached to the chin-cap and located in front of a mouth of the patient, the hook being configured to receive a tension-applying elastic element attachable to the patient's upper teeth in order to apply anterior traction to the maxilla, thereby correcting a class III malocclusion by pulling the maxilla forward and the mandible rearward.

These and other features of the present invention will become readily apparent upon further review of the following specification and drawings.

DETAILED DESCRIPTION OF THE PREFERRED EMBODIMENTS

Figure 1:
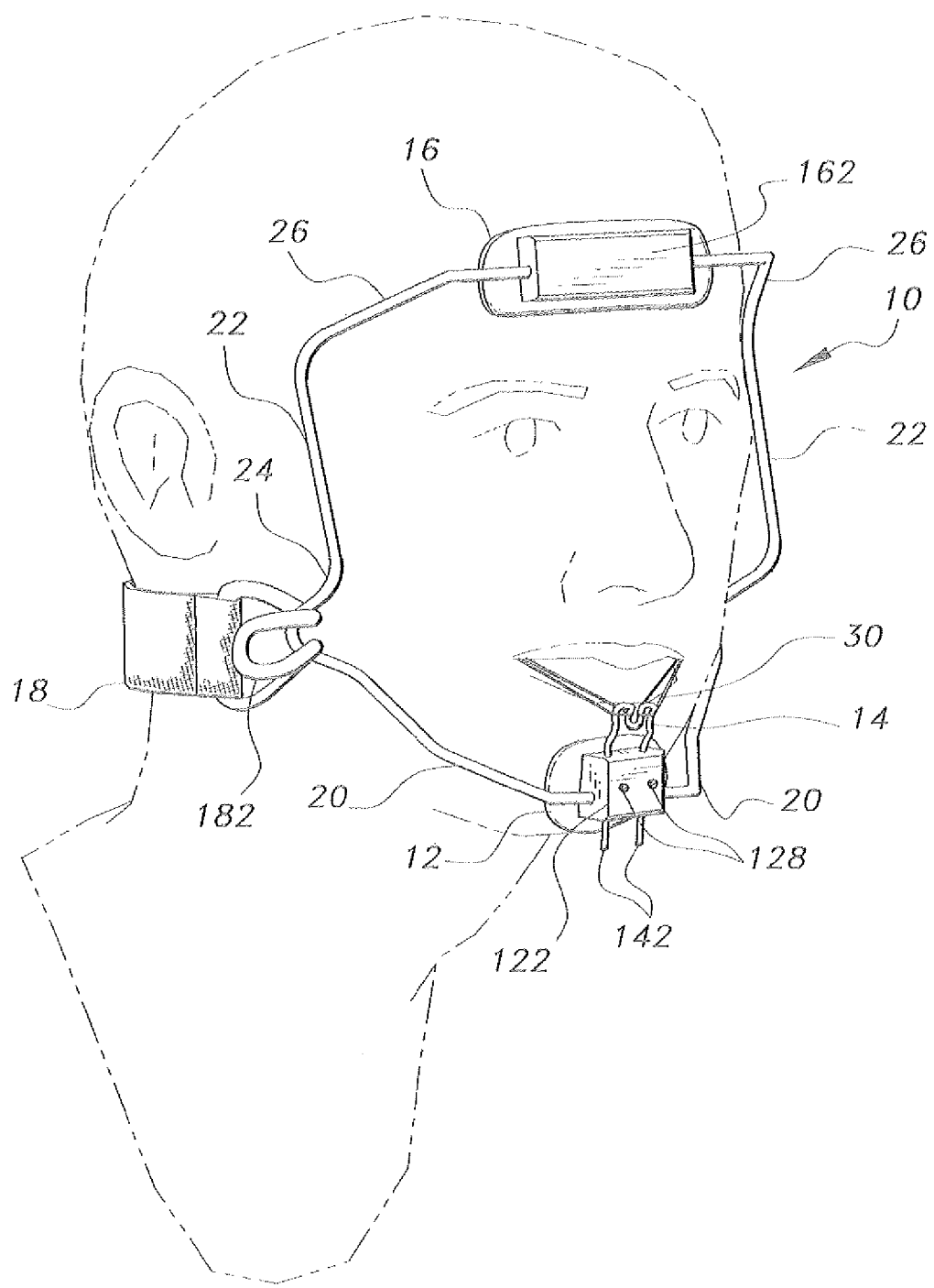
FIG. 1 is environmental perspective view of a reverse headgear with neck strap according to the present invention.
Figure 2:
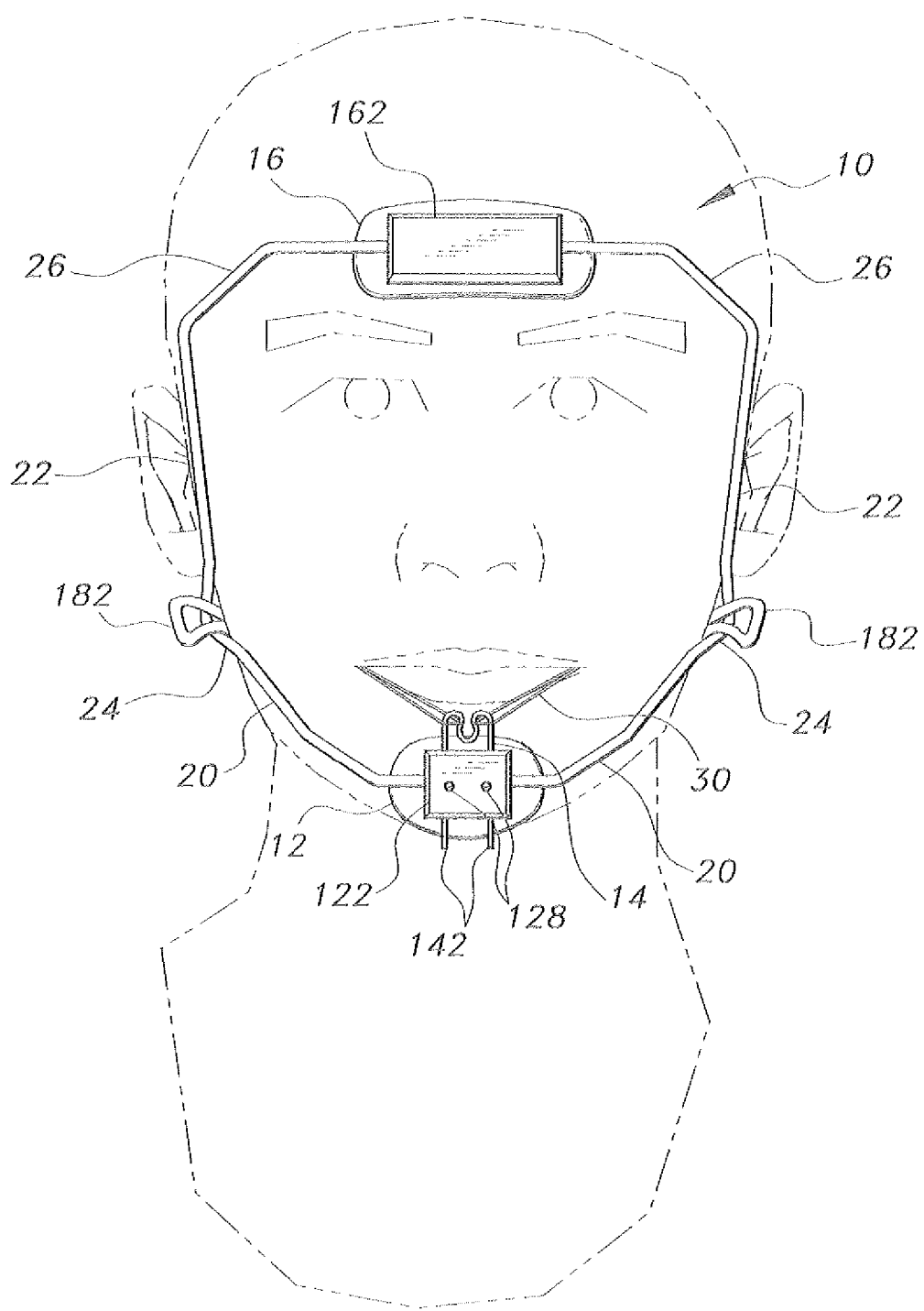
FIG. 2 is an environmental front view of the reverse headgear with neck strap of FIG. 1.
Figure 3:
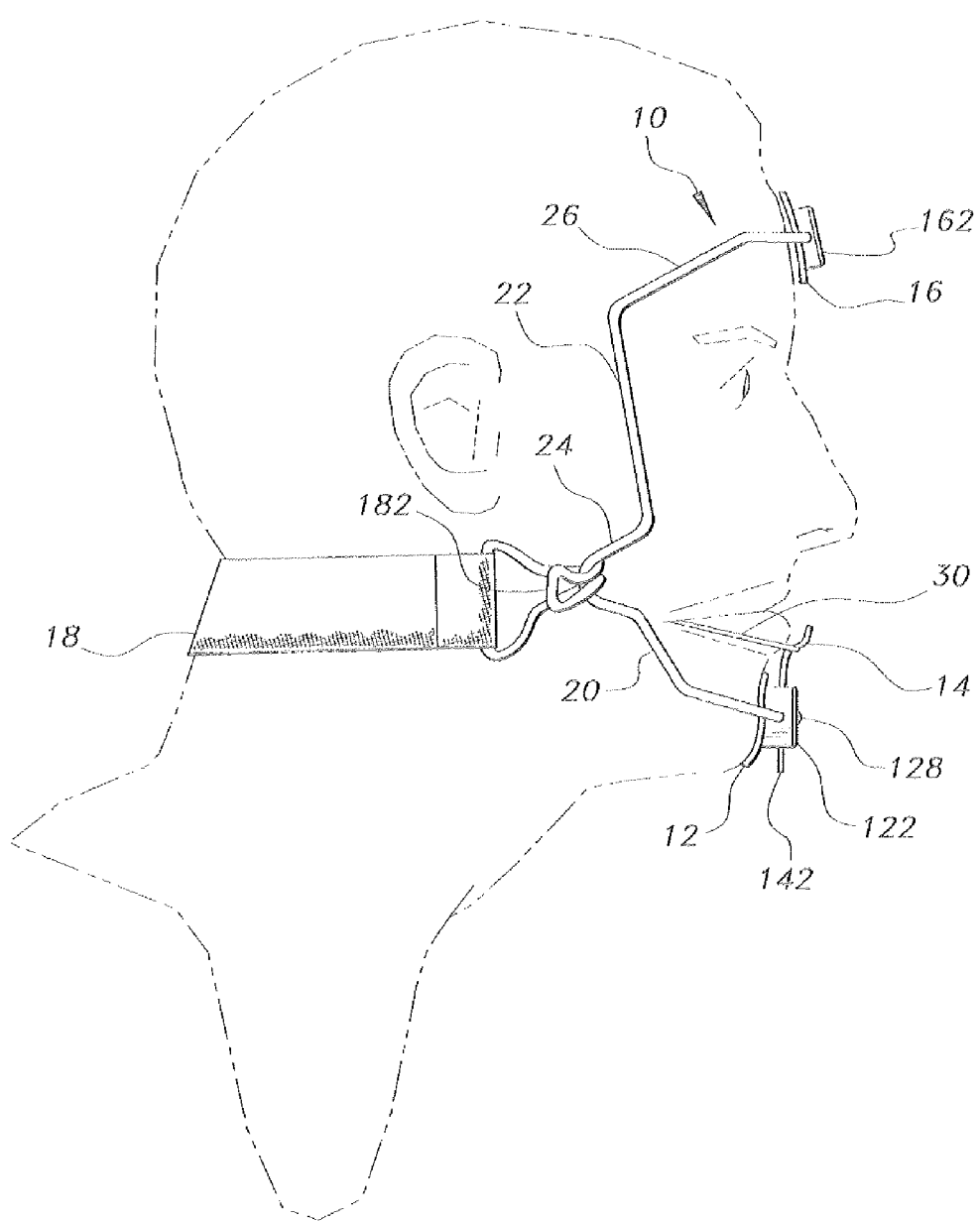
FIG. 3 is an environmental right side view of the reverse headgear with neck strap of FIG. 1.
Figure 4:
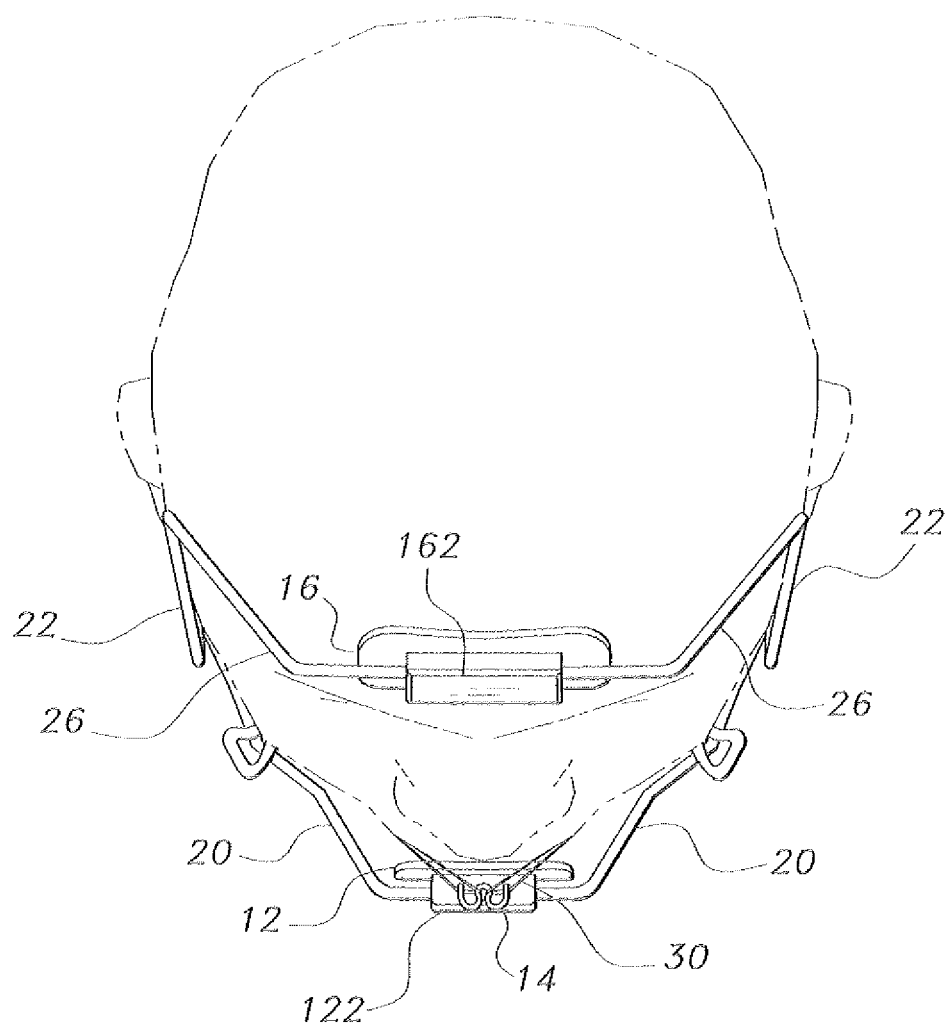
FIG. 4 is an environmental top view of the reverse headgear with neck strap of FIG. 1.
Figure 5:
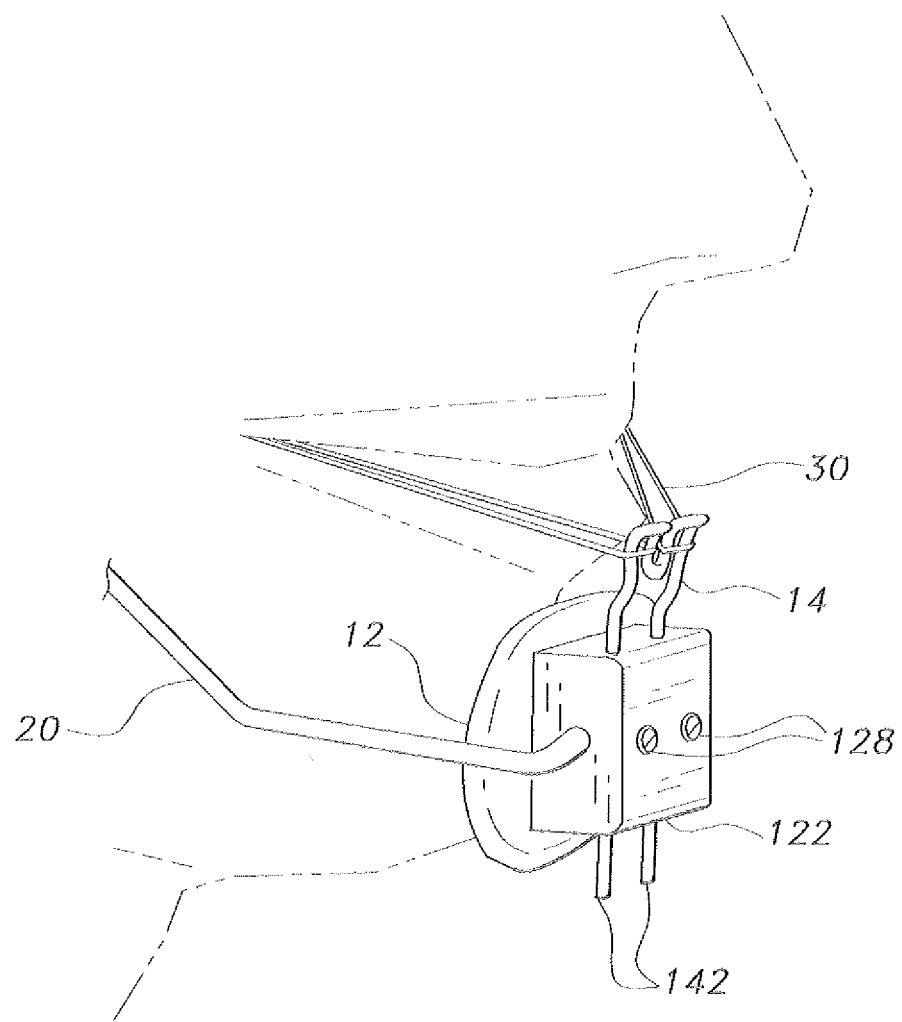
FIG. 5 is an environmental partial perspective view of the reverse headgear with neck strap of FIG. 1, showing details of the chin-cap and hook.

The reverse headgear with neck strap is orthodontic/facial orthopedic appliance that simultaneously applies an anterior traction force to the maxilla and a posterior traction force to the mandible for the correction of class III malocclusions.

An exemplary embodiment takes the form of a reverse headgear with neck strap, which, as depicted in FIGS. 1-5, includes a metal frame 10, a chin-cap 12 carrying a front hook 14, a forehead-cap 16 and a neck strap 18.

The metal frame 10 is a continuous metal framework made from wires or rods that outlines the periphery of the patient's face and has a pair of chin parts 20 in a lower portion of the frame, a pair of spaced side bars 22 each incorporating a bend 24 defining a rearward extending loop, and a forehead part 26 in the top portion of the frame. The metal frame 10 is made from stainless steel from round stock, either wire or rod, and a diameter that allows a limited amount of bending and adjustment of the frame 10 to adapt its configuration to the shape, length and width of the patient's face and head.

The chin parts 20 of the frame 10 supports the chin-cap 12 in the lower part of the frame 10, and the forehead part 26 of the frame 10 supports the forehead-cap 16 in the upper part of the frame. The side bars 22 extend from the patient's temples and alongside the checks to join the chin parts 20, so that the loops defined by the side bends 24 in the right and left side bars 22 of the frame 10 are located at a level below that of the patient's ears, about level with the patient's mandible, and are configured for connection with hook members 182 of the neck strap 18. The bends 24 also have second function in that they facilitate the above-mentioned bending and configuration of the frame 10.

The forehead part 26 of the frame 10 extends across the patient's forehead and has a central portion that is straight and sheathed within a tunnel or passage formed through a block 162 integral with the outer surface of the forehead-cap 16. The sheathing of this central part of the frame permits limited rotation of the forehead-cap 16 relative to the frame 10, thereby enhancing a comfortable fit on the patient's head and face. This relative movement of the forehead cap also facilitates the use of the forehead cap 16 and block 162 as a fulcrum, as will become better understood herein later.

In this particular instance, the free-ends of the chin parts 20 of the metal frame 10 are soldered together and imbedded inside a block 122, which is integral with the chin-cap 12. This stabilizes and prevents rotation of the chin-cap 12 relative to the chin parts 20 of the frame 10.

The bends 24 in the side bars 22 are arranged to point backward under the ears of the wearer and, as noted above, provide dual functions. That is, they provide sites receptive to bending forces for the vertical adjustment of the metal framework to allow a comfortable fit to the various sizes of the patient's face, while they provide places (viz., function as connection features) for the attachment of the neck strap 18 for applying posterior traction force to the mandible.

The chin-cap 12 is relatively rigid, having an inner surface shaped to fit and cup the patient's chin, and is lined by a foam pad or liner of soft material secured by suitable hypoallergenic adhesive or the like. The block 122 has bores defined therein that slidably receive the free-ends of the metal M-shaped front hook 124, which are secured by setscrews 128 to adjust the height of the front hook 124 so that it projects upwardly in front of the patient's mouth.

The front hook 14 is configured to permit the attachment of an elastic band or bands 30 (e.g., rubber bands), which is (are) stretched from the teeth of the patient in order to apply a traction force in forward direction with respect to the patient's head. The front hook 14 is, in this instance, comprising a single wire formed in an M-loop shape defining two adjoining peaks and two depending parallel legs 142. The two legs 142 of the front hook 14 are slidably disposed in the chin-cap block 122 for movement in the vertical direction and thus permit the adjustment of the front hook 14 to the correct position and bring the M-shape loop to an appropriate position relative to the patient's mouth. The front hook 14 can then be secured in the appropriate position by means of two tightening setscrews 128.

Figure 6:
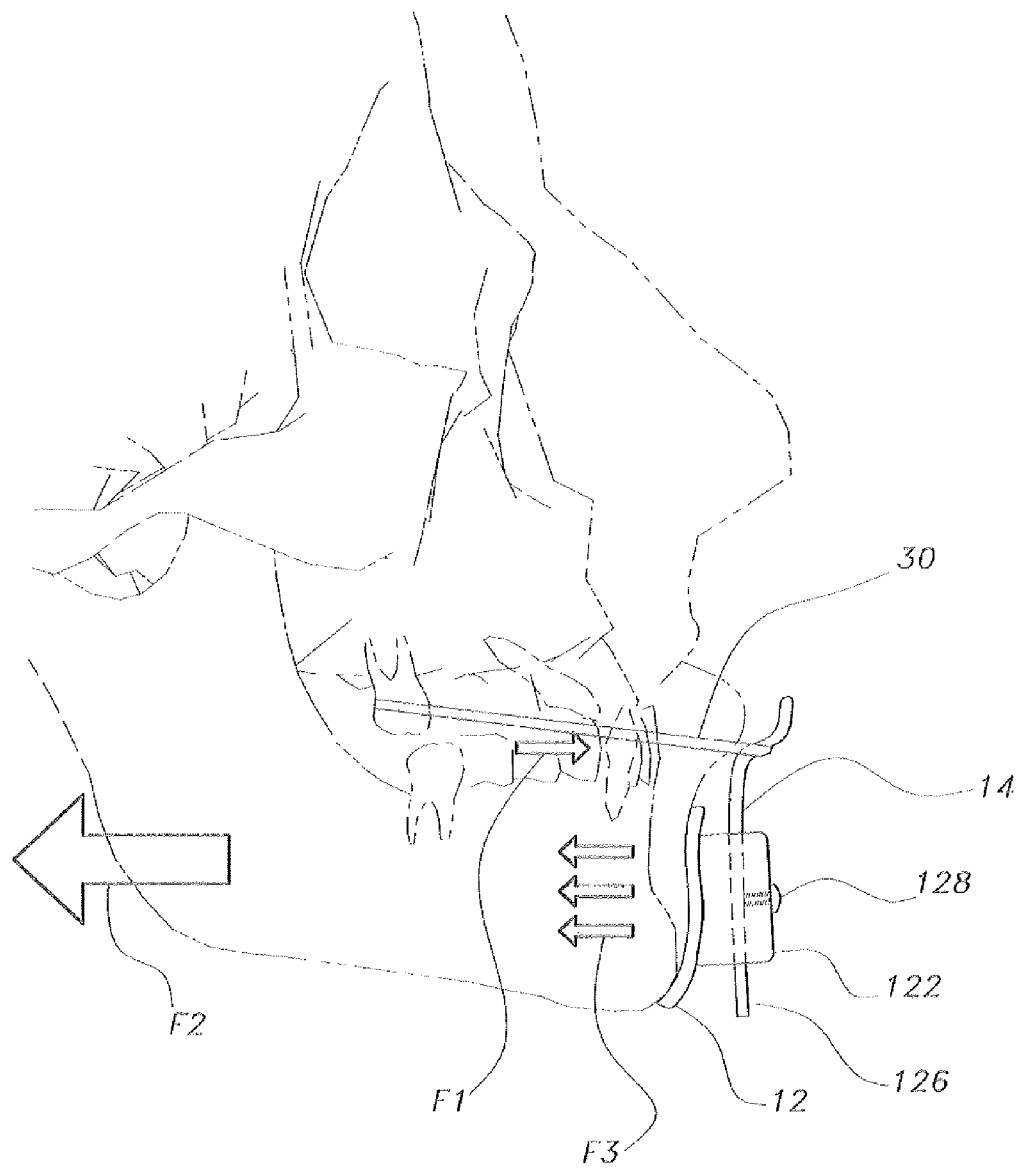
FIG. 6 is a diagrammatic environmental side view of the reverse headgear with neck strap of FIG. 1, showing exemplary forces exerted by the headgear.

The reverse headgear provides a single appliance that can simultaneously apply both anterior traction to the maxilla and posterior traction to the mandible, as shown by the directional arrows in FIG. 6. When the appliance is in use, the metal frame is adapted to the outline of the patient's face and to be laterally arranged in the illustrated manner with respect to the forehead, eyes, nose and mouth of the wearer. This provides a wide field of vision and does not interfere with the field of vision or eye movements of the patient. It also allows the wearing of spectacles.

The forehead-cap 16 is an assembly that includes the outer block 162, which may be slightly arcuate as it extends across the forehead in order to conform to curvature of the patient's forehead, and a foam pad or liner on the face bearing against the forehead. A film sheet may be applied to the patient's forehead beneath the forehead cap 16 for comfort, if desired. The block 162 has a bore extending therethrough so that the block 162 pivots or rotates on the forehead portion 26 of the frame 10 to adjust to the contour of the patient's forehead. The forehead portion 26 relative to the chin-cap 12 can be raised or lowered (adjusted) relative to the dimensions of the patient's head by adjusting the bend 24 in the side bars 22 to accommodate for long and short, wide and narrow faces. In addition, the vertical position of the M-hook 14 can be adjusted in relation to the patient's mouth and teeth by sliding the arms 142 of the front hook 14 to an appropriate position and securing it in position by the tightening screws 128.

A tension-applying means in the form of intra-oral elastic elements or bands 30, is connected between the M-shaped hook 14 and selected teeth of the patient such that the bands 30 are anchored by adjoining peaks of the hook 14 and pull or apply tension to the selected teeth, and therefore the upper jaw, in the direction of the front hook 14.

At the same time, the appliance contacts the patient's forehead and chin, and with the tension applied it by the neck strap 18, reacts in a manner wherein the forehead pad acts as fulcrum and levers the chin-cap 12 rearward, thus applying a force which acts on the mandible and mandibular teeth in a rearward or posterior direction relative to the patient's forehead. Irrespective of this rearward acting force, the bands 30 continue to pull the teeth to which they are connected, forward and toward the front hook 124.

The neck strap 18 can be made of a variety of materials having either a limited amount of elasticity or alternatively little or none. This allows the strap 18 to be tightened to the required degree and fastened in position, such as by the use of a Velcro® type hook and loop fastener to attach the hooks 182 to the strap 18 (which permits the strap 18 to be continuously adjustable to apply the desired degree of traction to the mandible, and to secure the reverse headgear to the patient's head), a double d ring arrangement or the like. The inner surface of the strap can be padded or suitably lined to facilitate prolonged contact with the wearer's neck.

FIG. 6 schematically depicts the forces discussed above and the direction in which they act in response to the neck strap 18 acting on the frame 10. More specifically, this illustration shows, by way of example, the intra-oral elastic stretch (F1) from upper first molar to the front hook 14 of the chin-cap 12. This applies force in the anterior direction to move the maxillary teeth and the maxillary bone forward in a growing patient. The chin-cap 12 applies force (F2) in the posterior direction force to the mandible and mandibular teeth from two sources. The first force (F1) is the reaction force from the intra-oral elastic. The second force (F2) is generated by the neck strap 18. The resultant force (F3) redirects the mandibular growth and affects the angulation and position of the lower incisors and the whole mandibular dental arch. The illustration shows the chin-cap 12 with the screws 128 (only one shown) tightened to set the vertical position of the front M-shape loop that will control the direction of force application resulted from the stretch of the intra-oral elastic between the molar hook and the front hook 14.

The reverse headgear with neck strap is particularly well suited for patients who are still growing, e.g., pre-teenage and teenage children. The traction force may assist new bone growth in the proper direction to correct for class III malocclusion. However, the device may also provide benefit for adults where the malocclusion may be due, in part, to poorly trained or rigid jaw muscles.

It is to be understood that the present invention is not limited to the embodiments described above, but encompasses any and all embodiments within the scope of the following claims.

I claim:

1. Reverse headgear with neck strap adapted to simultaneously apply anterior protraction force to the maxilla and posterior retraction force to the mandible, comprising:
    a forehead-cap adapted to engage a forehead of a patient;
    a chin-cap adapted to cup the patient's chin;
    a metal frame, the metal frame comprises a pair of frame members, each of the frame members having:
        i) a forehead portion adapted for extending across a patient's forehead;
        ii) side portions adapted for extending from the forehead portion alongside the patient's temples and cheeks on opposite side of the patient's head, the side portions defining rearward extending loops about even with the patient's mandible; and
        iii) chin portions extending from the loops, the chin portions being rigidly connected to opposite sides of the chin cap;
    a neck strap releasably connected to the rearward extending loops, the neck strap being adapted to pass behind the patient's neck to apply a traction force on the side portions of the frame to hold the forehead-cap and the chin-cap against the patient's forehead and chin, and to apply traction pulling the patient's mandible rearward; and
    a hook extending upward from the chin-cap, the hook being adapted for positioning in front of the patient's mouth, the hook being adapted to anchor tension applying elastic elements attached to the patient's upper teeth in order to apply anterior traction to the patient's maxilla simultaneously with the traction pulling the patient's mandible rearward.

2. The reverse headgear according to claim 1, wherein the hook is M-shaped and the chin cap has a pair of bores defined therein, the hook having legs slidable in the bores defined in the chin cap, the chin cap further comprising setscrews engaging the legs of the hook in order to selectively fix the height of the hook in front of the patient's mouth.

3. The reverse headgear according to claim 1, wherein the metal frame comprises a single frame member made from rod-shaped stock, said forehead cap having an outer block having a bore extending therethrough, the forehead portion of the frame extending through the bore in the block, said forehead cap pivoting on the block to adjust said forehead cap against the patient's forehead.

4. The reverse headgear according to claim 3, wherein said forehead cap further comprises a foam pad attached to said outer block, the foam pad being adapted for bearing against the patient's forehead for comfort.

5. The reverse headgear according to claim 1, wherein said outer block is slightly arcuate in order to conform to curvature of the patient's forehead.

6. The reverse headgear according to claim 1, wherein the metal frame is bendable to a degree sufficient to allow the frame to be adapted in shape to the patient's head.

7. The reverse headgear according to claim 1, wherein said neck strap is elongated, said neck strap further comprising hooks at opposite ends of said strap, the hooks releasably engaging the rearward extending loops of the side portions of said frame.

8. The reverse headgear according to claim 7, wherein said neck strap is made from an elastic material.

9. The reverse headgear according to claim 8, wherein said neck strap has mating releasable fasteners at opposite ends thereof, opposite ends of said strap extending through said hooks and being secured thereto by the mating releasable fasteners in order to adjust the length of said neck strap.

10. The reverse headgear according to claim 9, wherein said mating releasable fasteners comprise hook and loop fasteners, whereby said neck strap is continuously adjustable in length.

11. The reverse headgear according to claim 1, further comprising the tension-applying elastic elements.

\* \* \* \* \*